United States Patent
Madsen et al.

(10) Patent No.: US 6,265,882 B1
(45) Date of Patent: Jul. 24, 2001

(54) APPARATUS AND METHOD FOR MEASURING THE CONTENT OF INTRAMUSCULAR FAT IN CARCASSES OR PARTS THEREOF

(76) Inventors: Niels T. Madsen, Greve Bygade 26, DK-2670 Greve; Allan J. Rasmussen, Roeskovvej 3, DK-4250 Fuglebjerg; Claus Borggaard, Birkedevejen 20, DK-4130 Viby Sj.; Torben Nielsen, Strandjaegervej 21, DK-3630 Jaegerspris, all of (DK)

( * ) Notice: Subject to any disclaimer, the term of this patent is extended or adjusted under 35 U.S.C. 154(b) by 0 days.

(21) Appl. No.: 09/254,060

(22) PCT Filed: Jun. 19, 1998

(86) PCT No.: PCT/DK98/00260

§ 371 Date: Apr. 19, 1999

§ 102(e) Date: Apr. 19, 1999

(87) PCT Pub. No.: WO99/01754

PCT Pub. Date: Jan. 14, 1999

(30) Foreign Application Priority Data

Jul. 1, 1997 (DK) .................................................. 0779/97

(51) Int. Cl.[7] .......................... G01R 27/26; G01N 33/02
(52) U.S. Cl. ......................... 324/692; 324/693; 436/20; 436/21
(58) Field of Search .................................... 324/692, 693, 324/696, 709, 713, 715, 717, 71.1; 33/511, 558; 73/78; 436/20, 21, 60, 149

(56) References Cited

U.S. PATENT DOCUMENTS 2,763,935 * 9/1956 Whaley et al. ...................... 324/692
3,636,757 * 1/1972 Hansen ...................... 73/81
3,979,835 * 9/1976 Sumption et al. ...................... 33/558
4,252,130 * 2/1981 Le Pivert .............................. 324/692
4,270,274 * 6/1981 Hennessy ................................ 33/511

FOREIGN PATENT DOCUMENTS

3238400 * 4/1984 (DE) .
3 821 779 12/1989 (DE) .
2 298 923 9/1996 (GB) .
174 644 2/1994 (NO) .

OTHER PUBLICATIONS

Abstract of SU 1518–758 (as USSR Marin Hydro) Oct. 30, 1989, Derwent's abstract No. 90–252373/33, week 9033.

Slanger, W.D. and Marchello, M.J., "Bielectrical Impedance Can Predict Skeletal Muscle and Fat–free Skeletal Muscle of Beef Cow Primal Cuts," *Journal of Animal Science*, vol. 72, 1994, pp. 3124–3130.

* cited by examiner

*Primary Examiner*—Glenn W. Brown
*Assistant Examiner*—Vincent Q. Nguyen
(74) *Attorney, Agent, or Firm*—Marshall, O'Toole, Gerstein, Murray & Borun

(57) ABSTRACT

The apparatus for measuring the intra-muscular fat in carcasses or parts of carcasses or the total content of fat in minced meat has a first pair of electrodes for insertion into a carcass or part of a carcass or into minced meat. An alternating current (AC) generator is connected to these electrodes. Second and third pairs of electrodes are inserted parallel to the first pair. Both the second and third pairs have measurement circuits to measure the voltage and phase between the electrode pairs after insertion. The needle or bar shaped electrodes are tapered and insulated apart from 5–20 mm long free end sections. Electrodes are separated by 10–100 mm with each electrode 10–50 mm from the nearest of the first electrode pair. The portable unit for on-line use has a display output. The AC frequency applied to the first electrode pair may be changed in an exponential series to give different measurements.

8 Claims, 2 Drawing Sheets

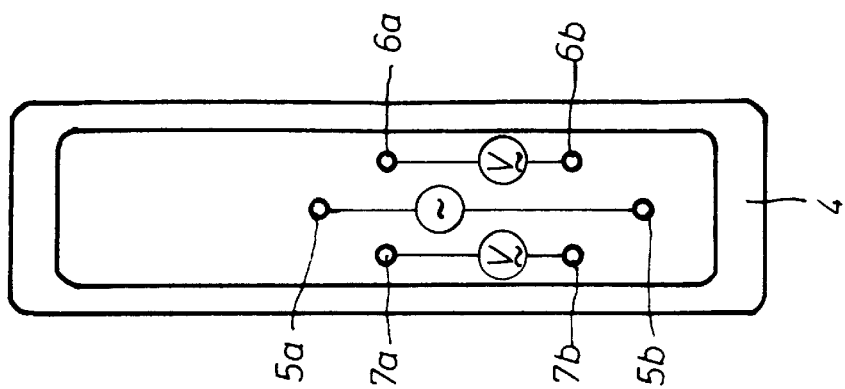
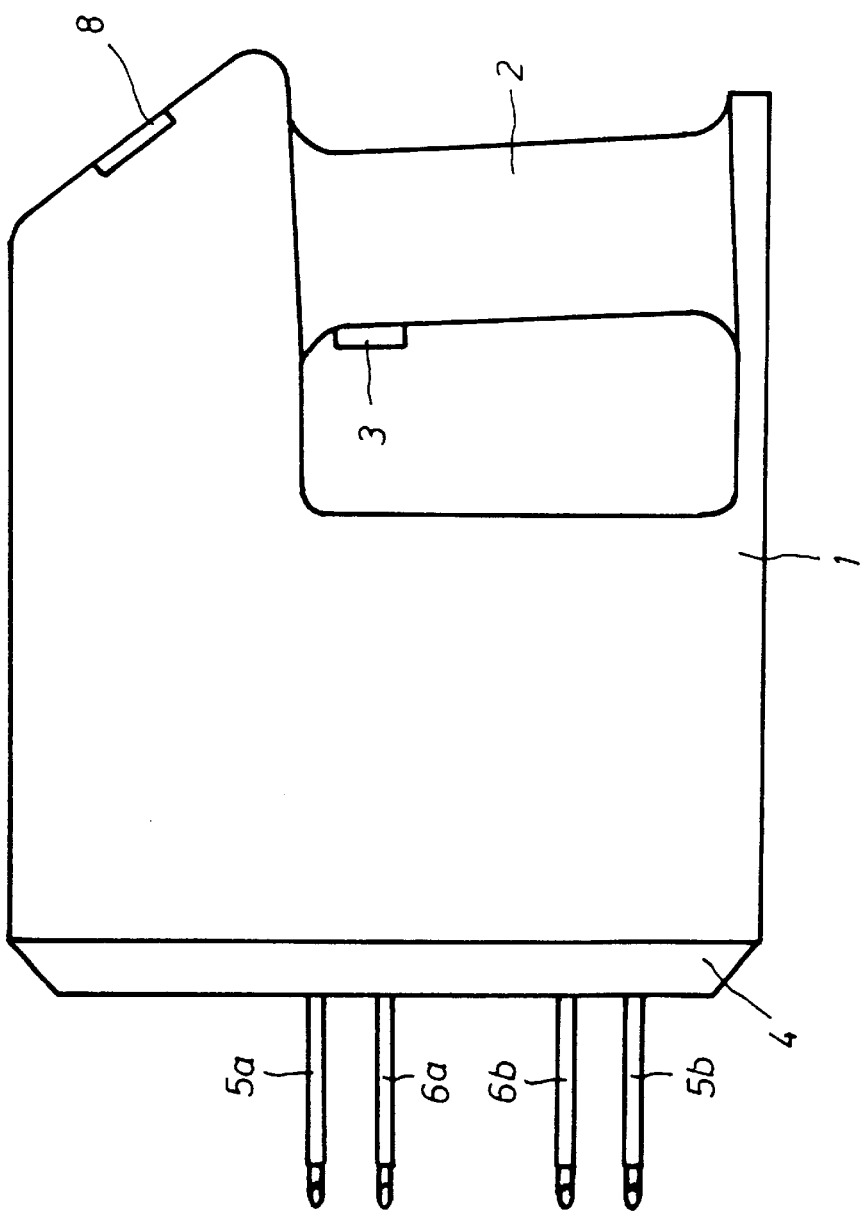

APPARATUS AND METHOD FOR MEASURING THE CONTENT OF INTRAMUSCULAR FAT IN CARCASSES OR PARTS THEREOF

BACKGROUND

1. Field of the Invention

The present invention relates to an apparatus for measuring the content of intramuscular fat in carcasses or parts thereof.

2. Description of the Prior Art

It is well known in the art that the content of intramuscular fat (fat marbling) in beef affects the taste and consistency of the meat. Muscles with a certain degree of fat in the muscles feels tender and juicy, whereas muscles without any fat give a tough and dry feeling. In order to be able to guarantee the tenderness and taste of the meat it is therefore important to be able to determine the content of intramuscular fat of muscles in carcasses or parts thereof.

It has recently been described that the fat content of beef muscles can be predicted by measuring the muscles' impedance (see article by W. D. Slanger and M. J. Marchello in J. Anim. Sci. 72 (1994), pp. 3124–3130: "Bioelectrical Impedance Can Predict Skeletal Muscle and Fat-free Skeletal Muscle of Beef Cow Primal Cuts"). The measurement is carried out by insertion of four electrodes into a muscle. Two of the electrodes are connected to an AC generator with a frequency of 50 kHz. The two other electrodes are placed between the first electrodes so that the four electrodes are aligned. The inner electrodes are connected to a circuit measuring the voltage over the electrodes and the phase in relation to the signal of the generator. On the basis of this measurement, the meat impedance can be determined (the impedance comprises a real component, which is pure ohmic resistance, and an imaginary component, which corresponds to the phase shift). The impedance correlates to the muscle's fat content and it is thus an expression of the amount of intramuscular fat in the muscle.

The reason why four electrodes are used for the measuring is that the contact resistance between electrodes and meat is very high and may vary considerably depending on the pH and liquid content of the meat. When a constant alternating current is passed through the outer electrodes, measurements can be taken over the inner electrodes by means of a phase and amplitude detector having very high input impedance. This has the effect that the fall in voltage in the transition between the inner electrodes and the meat becomes relatively small as no current is drawn in the measuring. Variations in the contact resistance are therefore insignificant.

The above-mentioned test equipment is unsuitable for on-line measuring of intramuscular fat in abattoirs or meat processing plants. It is for instance not sufficiently reliable to comply with the requirements imposed on such equipment to allow it to be used in abattoirs to determine fat marbling.

The purpose of the invention is therefore to provide an apparatus suitable for measuring intramuscular fat under the operational conditions of abattoirs or meat processing plants. Preferably the apparatus should also be able to determine the fat content of minced meat.

SUMMARY OF THE INVENTION

The apparatus according to the invention comprises:
a first pair of electrodes consisting of two parallel insertion electrodes,
an AC generator which is connected to these electrodes,
a second pair of electrodes consisting of two insertion electrodes placed parallel to the first insertion electrodes,
a measuring circuit designed to measure the voltage and phase of the second pair of electrodes after the electrodes have been inserted into a muscle in the carcass or part thereof or into the minced meat,
a third pair of electrodes consisting of two insertion electrodes which are placed parallel to the other electrodes and
means for measuring the voltage and phase of this third pair of electrodes after they have been inserted into the muscle or minced meat.

The apparatus according to the invention has important advantages compared with the above-mentioned test equipment and these advantages make it suitable for use in the conditions prevailing in abattoirs. Firstly, the third pair of electrodes permits double measuring of the impedance, and tests show that this double measuring is able to bring the accuracy to a satisfactory level. The operator's work is thereby the same as if he were to use equipment with only one pair of measuring electrodes; he just has to move the apparatus towards the carcass so that the electrodes are inserted into the muscle. When double measuring is carried out by insertion of probes or the like into meat, it is important to avoid measuring in the same hole or area, as this could result in considerable errors. Likewise, it is important that both measurements are taken within the area of the muscle where the most reliable results are obtained. With the apparatus according to the invention, both these conditions are considered. Consequently, the apparatus of the invention not only saves labour in comparison to the traditional double-measurement technique, but the operator does not have to concentrate any harder during insertion as the points of insertion are by definition different and are in advance separated by a desired distance, given by the distance between the two pairs of measuring electrodes.

An additional advantage of the use of two pairs of measuring electrodes is that the two measuring results can immediately be compared and the measurement discarded if they differ considerably from each other. This could for instance be the case if an electrode hits a fat pocket.

For measurement of the intramuscular fat content, the electrodes are inserted into a muscle in the carcass or part thereof. In the present description the designation a "muscle" may include several coherent muscles. In the broadest sense a "muscle" may be a fleshy part or a lean meat region of the carcass or part thereof.

The apparatus according to the invention can also be used for measuring the total content of fat in minced meat from a carcass or carcass part, as the electrodes are inserted into the minced meat. Preferably, this is compacted to achieve good contact between the particles of the material. Using the apparatus according to the invention, butchers and in-store butchers can for instance quickly and cheaply determine the fat content in minced meat.

It should be mentioned that the apparatus according to the invention may comprise a fourth, fifth or even more pairs of electrodes for the measuring, but preferably the apparatus only has three pairs of electrodes as these have proved to provide sufficiently accurate results, allow direct comparison of the signals and give a simple design of the apparatus.

Advantageous embodiments of the apparatus according to the invention are described below:

The insertion electrodes preferably have a tapered free end designed for insertion into the carcass, the carcass part or the minced meat to be measured and a mounting end at which they are fitted in the apparatus.

The insertion electrodes are preferably needle or bar shaped, and are equipped with an electrically insulating jacket except for a section close to the insertion end where preferably 5 to 20 mm are bare.

Preferably, the diameter of the electrodes is 2 to 5 mm and the length 25 to 150 mm.

The apparatus preferably comprises a stop device designed to limit the insertion depth of the electrodes into the carcass, the carcass part or the minced meat, usually in the form of a plate at right angles to the electrodes.

The electrodes are usually placed in a hexagonal pattern with the electrodes of the first pair of electrodes placed in opposite apexes in the hexagon, the electrodes of the second pair of electrodes placed in two other adjacent apexes and the electrodes of the third pair of electrodes placed in the two remaining apexes.

Alternatively, the second and the third pair of electrodes may be placed in the apexes on a rectangle and the first pair of electrodes be placed in the area of the rectangle on the long center line of the rectangle.

The distance between the second pair of electrodes and the third pair of electrodes is preferably between 0.2 and 1 times the distance between the two electrodes of the first pair of electrodes, preferably between 10 and 100 mm.

The three planes containing the two insertion electrodes of the first, second and third pairs of electrodes are preferably parallel, and the second and third of these planes are preferably on either side of the plane containing the first pair of electrodes, preferably with the same distance to the plane.

A further embodiment is characterised in having mainly the same distance from each of the electrodes in the second and third pairs of electrodes to the closest electrode in the first pair of electrodes, preferably a distance of between 10 and 50 mm.

The apparatus according to the invention is preferably designed as a portable hand-held measuring equipment with a housing on one side of which a handle is designed and on the other side of which the parallel placed insertion electrodes are fitted, and preferably, it contains a calculation unit for interpretation of the measurements and possible a unit for display of the results regarding the content of intramuscular fat of the individual carcasses or carcass parts, or the total content of fat in minced meat and/or for temporary storage of these results.

The apparatus may have devices for changing the generator frequency and for measuring at various frequencies, preferably in the area between 25 and 100,000 Hz. Experience shows that this may result in improved measurement accuracy. It is for instance possible to measure at 5 to 20 different frequencies. Certain frequencies have proved to provide better correlation between impedance and fat content than other frequencies.

The invention also relates to a method for measuring the content of intramuscular fat in carcasses or parts thereof or the total content of fat in minced meat. The method according to the invention comprises:

insertion into a muscle in a carcass or part thereof or into minced meat of a first pair of electrodes consisting of two parallel insertion electrodes connected to an AC generator, insertion into the muscle or the minced meat of a second pair of electrodes consisting of two insertion electrodes placed parallel to the first electrodes, measuring of the voltage and phase of the second pair of electrodes while the electrodes are in the muscle or the minced meat, insertion into the muscle or the minced meat of a third pair of electrodes consisting of two insertion electrodes placed parallel to the other electrodes, and measuring of the voltage and phase of the third pair of electrodes while in the muscle or minced meat.

In an embodiment of the method, the electrodes are inserted simultaneously into the carcass, the carcass part or the minced meat.

In a preferred embodiment of the method according to the invention the frequency of the generator is changed and the voltage and phase of the second and third pairs of electrodes is measured at different frequencies.

Preferably, measurements are taken in the frequency area between 25 and 100,000 Hz.

Measurements can especially be taken at different frequencies constituting a mainly exponential serie such as a serie consisting of frequencies whose individual elements constitute a doubling of the frequency of the previous element in the serie.

In the present description carcasses and carcass parts are preferably cattle carcasses or cuts of these such as pistols, hindquarters or other cuts. Minced meat is especially minced beef.

BRIEF DESCRIPTION OF THE SEVERAL VIEWS OF THE DRAWING

The invention is described in more detail below with references to the drawings wherein:

FIG. 1 shows a hand-held measuring equipment according to the invention for measuring the content of intramuscular fat in carcasses or parts thereof or the total content of fat in minced meat, FIG. 2 shows the same equipment viewed from a different angle in the direction of the equipment's insertion electrodes and FIG. 3 shows a diagram of measuring results obtained by determining the intramuscular fat content of muscles by a standard laboratory analysis and by the present impedance measuring method.

DETAILED DESCRIPTION OF THE PREFERRED EMBODIMENT

Figure 3:
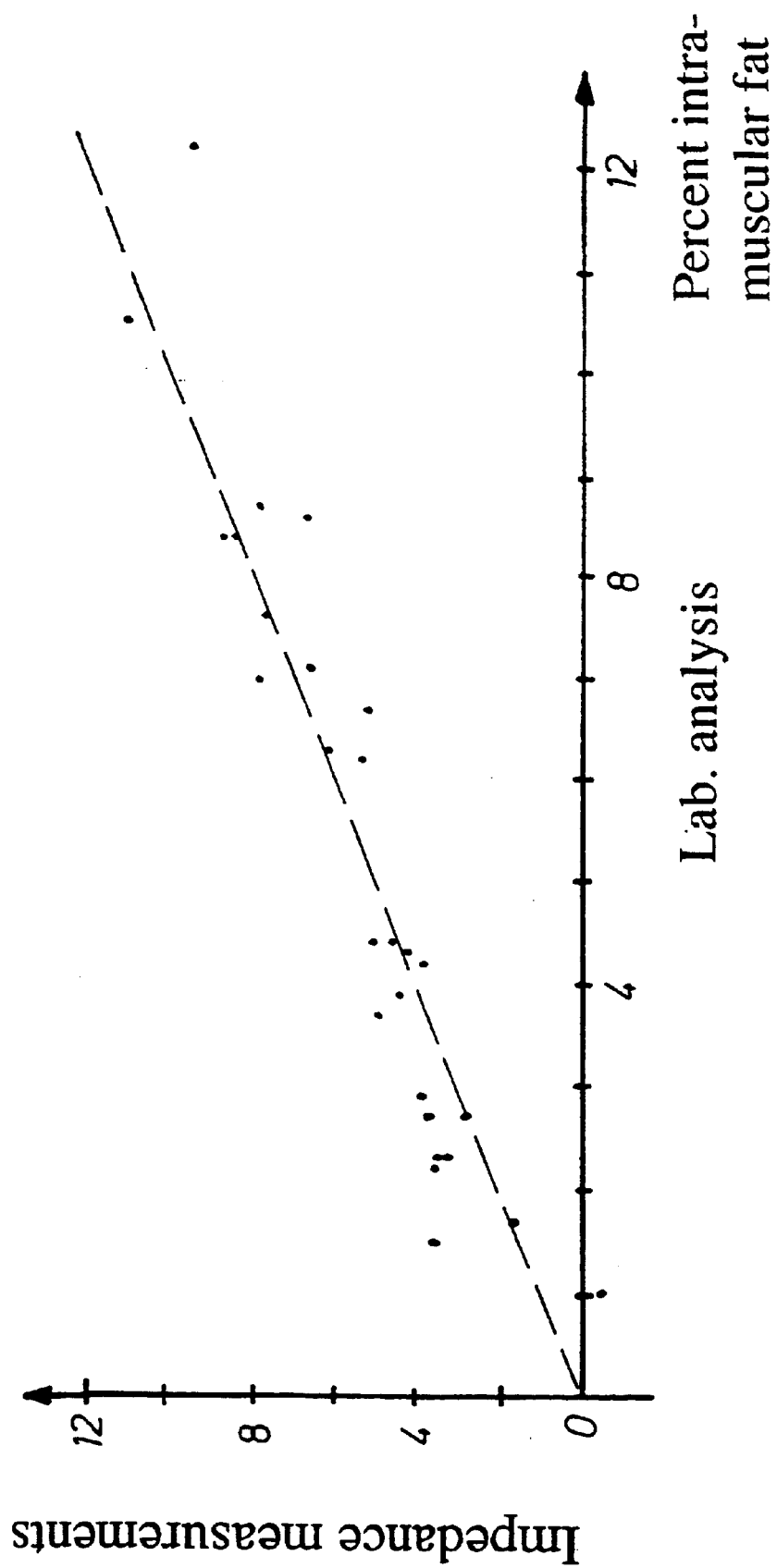

The measuring equipment of FIGS. 1 and 2 comprises a housing 1 with six insertion electrodes on one side and a handle 2 with a control button 3 on the other side. The electrodes consist of 3 mm thick and 45 mm long bars of a chrome-nickel alloy. The bars have a bevel-edged point at one end to give them a cutting edge. The electrodes are mounted on a front plate 4 of plastic. The plate with the electrodes is fitted to the housing in such a way that it is easily replaceable if the electrodes are bent. The electrodes are insulated, for instance powder lacquered, except for the bevel-edged outermost section, which serves as the contact surface. As can be seen in FIG. 2, the electrodes are placed in a hexagonal pattern. They form three pairs of electrodes of which the first pair 5a, 5b is connected to an AC generator fitted in the housing 1 and which supplies constant alternating current. The other pair of electrodes 6a, 6b is connected to the input of a circuit fitted in the housing which measures the voltage across the electrodes and the phase in relation to the signal of the AC generator. The third pair of electrodes 7a, 7b is connected to a second input of the circuit for measuring the voltage across the electrodes and the phase in relation to the signal of the AC generator. During measurement, the first and second inputs are cut in alternately (multiplexing). Instead of one circuit with two changeable inputs, there may be two circuits each with its own input which is constantly connected to electrode pair 6a, 6b and electrode pair 7a, 7b.

The AC generator and the measuring circuit are fitted on a printed circuit in the housing 1. The printed circuit also comprises a control and calculation unit (computer) with a loaded measuring program. The unit can set the AC generator to various, previously defined frequencies and alternately couples electrode pairs 6a, 6b and 7a, 7b to the input of the measuring circuit which comprises an A/D converter and a phase detector. The unit stores the digital measuring values obtained and interprets the stored sets of measuring values by means of a built-in algorithm expressing the content of intramuscular fat or the total content of fat as a function of the impedance measured. The unit sends the result to an alphanumerical display 8 which can be read by the operator.

Furthermore, the control and calculation unit comprises an program routine which picks up any erronenous measurements. Via the display it instructs the operator to repeat the measuring if this is erroneous. The routine compares for instance the signals from the electrode pair 6a, 6b with the signals from the electrode pair 7a, 7b. If the signals differ considerably, an error message will be given and the measuring is repeated.

The control and calculation unit is connected to a plug which is not used during measuring but is hidden under a plate in the housing. Using the plug, the equipment can be connected to a main computer or a network and stored measuring data or results can thus be transferred to a main computer where they can be used (perhaps together with other data on the carcasses or carcass parts in question) for instance for sorting of the carcass or the carcass parts or for payment of the supplier according to the degree of marbling.

As a supplement to the plug, the measuring equipment can have an infrared transmitter/receiver for wireless transmission of data to and from a fixed communication unit which is connected to a main computer. In this way, the equipment can be made completely independent of wiring and can be carried freely and used anywhere in the plant.

The equipment housing contains a battery which supplies the necessary electric energy.

The measuring equipment is very simple to use:

The operator inserts the six electrodes into a predetermined part of the carcass or the cut or into the minced meat until the plate 4 rests against the surface of the item. The operator then activates the button 3 which actuates a switch; this in turn starts a measuring procedure which is carried out by the control and calculation unit. The result of the measuring and calculations is available within a second. The muscle's intramuscular fat content/degree of fat marbling or the minced meat's total fat content is shown on the display 8 and is stored in the unit memory where it can later be retrieved, if necessary, via the plug or the infrared transmitter/receiver, if this is available.

The housing may be fitted with a keyboard for manual input of relevant data, for instance the serial number of the carcass and perhaps the animal's slaughter weight, breed or age or other data which may be relevant for the measured item in question. Likewise, the housing may have an input port for a bar code scanner for identification of the carcass, the carcass part or the batch of minced meat.

EXAMPLE

The present example shows that the content of intramuscular fat in the loin muscle of cattle carcasses may be determined by impedance measuring. The example also shows that accuracy is improved considerably when a double determination is performed. For calculation of the fat content, measurements are performed at 10 different frequencies in the interval 50–50,000 Hz.

Measuring is carried out by means of impedance measuring equipment with four insertion electrodes. The equipment comprises a first pair of electrodes consisting of two insertion electrodes. They are connected to an AC generator providing a constant alternating current of 800 $\mu$A. Furthermore, it has a second pair of electrodes, which is placed between the said electrodes and are connected to a circuit measuring voltage and phase.

The measurements are carried out on intact cattle carcasses at a predetermined time after the shooting. The electrodes are inserted into the loin muscle at the fifth and sixth lumbar vertebra. Measurements are taken at for instance the following 10 frequencies (Hz):

| 56 | 100 | 223 | 889 | 1774 |
|---|---|---|---|---|
| 2812 | 5612 | 19906 | 22335 | 50002 |

To ensure that the measured muscles include a sufficiently broad variation as regards the content of intramuscular fat, measurements are taken on a representative number of carcasses. From these carcasses meat samples are taken and the fat content is determined by a standard laboratory analysis.

The impedance (voltages and phase shifts) measured for the selected carcasses are entered into algorithms developed to express the intramuscular fat content. The following formula is used:

$$IMF = c + \sum_{i=1}^{n} \text{Re}_i \cdot a_i + \sum_{i=1}^{n} \text{Im}_i \cdot b_i$$

in which IMF is the intramuscular fat percentage; n is 10; $a_i$, $b_i$ and c are constants; and $\text{Re}_i$ is the real value of the impedance (corresponding to the voltage or the ohmic resistance) and $\text{Im}_i$ is the imaginary value of the impedance (corresponding to the phase shift) at frequency i. If two insertions are used, IMF is calculated for each insertion after which the true IMF is found as the mean value. Finally, the IMF values thus calculated are compared with the analytically found values and the correlation coefficient R is found. This turns out to be 0.84 for one insertion and 0.93 for two insertions. The average error in using impedance measuring instead of fat analysis is 1.53% for one insertion and 1.08% for two insertions.

The results of the analysis and impedance measurements (with two insertions) is shown in FIG. 3. It shows good agreement between the two measuring methods. Double impedance measuring performed with the present measuring equipment is therefore a cheap and simple alternative to the expensive and labour-consuming laboratory analysis. The equipment may be used on-line in abattoirs and almost instantaneously provides a measurement result that can be compared with the result obtained through a traditional laboratory analysis.

We claim:

1. An apparatus for measuring the content of intramuscular fat in carcasses or parts thereof or the total content of fat in minced meat, comprising:

a first pair of electrodes consisting of two parallel insertion electrodes (5a, 5b) which protrude from a plate (4);

an AC generator connected to said electrodes to generate a current in a muscle in a carcass or part thereof or in minced meat after the electrodes have been inserted in the muscle or minced meat;

second and third pairs of electrodes, each of said pairs consisting of two insertion electrodes (6a, 6b), which are placed parallel to the first pair of insertion electrodes (5a, 5b) and protrude from the same plate (4), the electrodes of the second and third pairs of electrodes (6a, 6b; 7a, 7b) being arranged symmetrically about a line defined by the two electrodes of the first pair of electrodes; and means of measuring the voltage and phase of the second and third pairs of electrodes (6a, 6b; 7a, b) individually after the electrodes have been inserted into the muscle or into minced meat and the muscle or minced meat is exposed to the current of the first pair of electrodes.

2. Apparatus according to claim 1, wherein the insertion electrodes (5a, 5b, 6a, 6b, 7a, 7b) have a tapered free end designed for insertion into the carcass or part thereof or the minced meat to be measured and a mounting end at which they are fitted in the apparatus.

3. Apparatus according to claim 1, wherein the insertion electrodes are mainly needle or bar shaped and are equipped with an electrically insulating jacket except for the section closest to the insertion end where preferably 5 to 20 mm are bare.

4. The apparatus according to claim 1, said apparatus being a portable hand-held measuring device with a housing (1) on one side of which a handle (2) is designed and on the other side of which the parallel insertion electrodes (5a, 6b, 6a, 6b, 7a, 7b) are fitted, and further including a calculation unit for interpretation of the measurements and a unit (8) for display of the results for the content of intramuscular fat in the individual carcasses or parts thereof or the total content of fat in minced meat.

5. A method for measuring the content of intramuscular fat in carcasses or parts thereof or the total content of fat in minced meat, comprising:

inserting into a muscle in one of a group including a carcass, a part of said carcass, and minced meat, of a first pair of electrodes consisting of two parallel insertion electrodes (5a, 5b), which are connected to an AC generator to generate a current in one of a group including the muscle and minced meat;

inserting into the one of the group including the muscle and the minced meat, of second and third pairs of electrodes each consisting of two insertion electrodes (6a, 6b; 7a, 7b), which are placed parallel to the first pair of electrodes (5a, 5b); and measuring the voltage and phase of the second and the third pairs of electrodes (6a, 6b; 7a, 7b) individually while the electrodes are inserted into the one of the group including the muscle and the minced meat, and said one of the group including the muscle and the minced meat is exposed to the current of the first pair of electrodes (5a, 5b).

6. Method according to claim 5, wherein the electrodes (5a, 5b, 6a, 6b, 7a, 7b) are inserted simultaneously in the carcass or part thereof or into the minced meat.

7. Method according to claim 5, wherein the frequency of the generator is changed and the voltage and phase of the second and third pairs of electrodes are measured at different frequencies.

8. Method according to claim 6, wherein measuring is carried out at different frequencies constituting a mainly exponential series, such as a serie consisting of frequencies whose individual elements constitute a doubling of the frequency compared with the preceding element in the serie.

* * * * *